United States Patent [19]

Kupriyanovich

[11] 4,289,121

[45] Sep. 15, 1981

[54] METHOD FOR CONTROLLING FUNCTIONAL STATE OF CENTRAL NERVOUS SYSTEM AND DEVICE FOR EFFECTING SAME

[76] Inventor: Leonid I. Kupriyanovich, ulitsa Dunaevskogo, 4, kv. 61, Moscow, U.S.S.R.

[21] Appl. No.: 71,854

[22] Filed: Sep. 4, 1979

[30] Foreign Application Priority Data

Nov. 26, 1978 [SU] U.S.S.R. ............................ 2686052

[51] Int. Cl.³ .......................................... A61M 21/00
[52] U.S. Cl. ................................................. 128/1 C
[58] Field of Search ..................................... 128/1 C

[56] References Cited

U.S. PATENT DOCUMENTS

| | | | |
|---|---|---|---|
| 3,470,870 | 10/1969 | Schoffer | 128/1 C |
| 3,576,185 | 4/1971 | Schulz et al. | 128/1 C |
| 3,773,049 | 11/1973 | Rabichev et al. | 128/1 C |

FOREIGN PATENT DOCUMENTS

| | | | |
|---|---|---|---|
| 1183607 | 12/1964 | Fed. Rep. of Germany | 128/1 C |
| 1220031 | 1/1960 | France | 128/1 C |
| 160776 | 1/1963 | U.S.S.R. | 128/1 C |

*Primary Examiner*—William E. Kamm
*Attorney, Agent, or Firm*—Lackenbach, Lilling & Siegel

[57] ABSTRACT

The method consists of subjecting the central nervous system to the effects of rhythmic audio and light signals which are applied simultaneously in accordance with biorhythms corresponding to a stable state of the central nervous system. After setting the initial light and audio signals, the frequency, amplitude and duration of the rhythmic light and audio signals are varied in synchronism according to frequency variations of the biorhythms. The method is carried out with the aid of a device comprising a light pulse pacemaker, an audio pulse pacemaker, pulse frequency, duration and amplitude setting units, modulators of signals produced by the pacemakers, which are controlled by the setting units, and a switch intended to determine the direction of variation of audio and light signals. The device also includes a programming unit to receive information on the state of the central nervous system.

14 Claims, 5 Drawing Figures

METHOD FOR CONTROLLING FUNCTIONAL STATE OF CENTRAL NERVOUS SYSTEM AND DEVICE FOR EFFECTING SAME

FIELD OF THE INVENTION

The present invention relates to medicine and, more particularly, to a method and device for controlling the functional state of the central nervous system.

The invention is effective in inducing sleep or making it deeper, as well as in raising the level of wakefulness; it also helps against insomnia and in cases of abnormal sleepiness.

BACKGROUND OF THE INVENTION

The rapid development of science and technology, the information explosion and the necessity to keep pace with the times all have had a tremendous impact on the central nervous system. The resultant stresses almost invariably lead either to superexcitation or to abnormal sleepiness and strongly affect people's health and working capacity.

Drugs that are often used in such cases normally contain toxic narcotics. Prolonged courses of drug therapy may result in habit formation so that the patient has to be given higher doses or more potent drugs.

A number of attempts have been made to dispense with drug therapy by exposing the central nervous system to the effects of such physical phenomena as light or sound. For example, there is known a method which makes use of regularly repeated light and audio effects, such as the sound of ocean breakers or the monotonous noises of rain. The method produces inhibition of the cerebral cortex and sometimes makes a patient fall asleep, but it is not effective enough to reestablish normal sleeping habits and thus eliminate abnormalities of biorhythms which cause sleeplessness or, on the contrary, make a person sleepy during the day.

The method under review largely depends on the psychophysilogic state of an individual and at times may prove to be ineffective. There have been attempts to combine the effects of monotonous audio and light signals; although more effective than the foregoing method, such attempts have not produced consistently good results. It can thus be inferred that monotonous signals are not the ultimate solution. It was then found that the action on the central nervous system could be intensified by varying the frequency, duration and amplitude of signals according to an electroencephalogram. Unlike monotonous signals, signals with varied parameters are more effective in altering the biorhythmic pattern and eliminating sleep distrubances. Yet the positive effect of such treatment cannot be maintained over a prolonged period of time.

The latter method is effected with the aid of a device comprising a controlled audio pulse pacemaker, a controlled light pulse pacemaker, and a unit for controlling the two pacemakers according to variations of bioelectric currents of the brain recorded during sleep. The device has all the disadvantages inherent in the method which it is intended to carry out. It must further be pointed out that none of the known devices of this type are capable of controlling the level of wakefulness.

SUMMARY OF THE INVENTION

It is an object of the present invention to provide a method for controlling the functional state of the central nervous system, which would ensure a stable and prolonged effect on the human organism.

It is another object of the invention to provide a method for controlling the functional state of the central nervous system, which could be used to rapidly induce profound sleep.

It is still another object of the invention to provide a method to ensure strict correlation between the state of the organism and the effects of signals acting on the organism to change the biorhythms.

It is a further object of the invention to provide a method which could make it possible to control the degree of wakefulness and eliminate sleepiness.

It is an important object of the invention to provide a device for controlling the functional state of the central nervous system of both sleeping and wakeful patients.

The foregoing and other objects of the invention are attained by providing a method for controlling the functional state of the central nervous system by exposing a patient to simultaneous effects of a rhythmic audio signal and a rhythmic light signal and determining the change of the frequency of the biorhythms in the course of the transition to one of the extreme stable states of the central nervous syrtem. This is followed by setting an initial light signal and an initial audio signal and synchronously varying the frequency, amplitude and duration of the rhythmic light and audio signals within the established intervals of the frequency variation of the biorhythms. The tonality of the audio signal and chromaticity of the light signal are varied according to changes of the intervals.

The invention is based on the established fact that the effects of light and audio pulse signals are more pronounced if these signals change according to variations of biorhythms caused by changes in the state of the central nervous system. The invention stresses the necessity of using signals of varying color and tonality instead of monochrome and monotonous signals. The color and tonality of the signals are to varied according to changes of the frequency, amplitude and duration of the biorhythm, as well as according to the interaction between the light and audio signals.

The method according to the invention is advantageous in that it is carried out with due regard for the original psychophysiologic state of the patient and in that the change of the functional state of the central nervous system is a reflection of the actual state of the patient. The reason for this lies in the fact that the rhythmic light and audio signals are directly related to biorhythms of the organism.

It is expedient that the chromaticity and tonality of the initial signals should be chosen by the patient so as to make sure that the initial rhythmic signals closely correspond to the actual psychophysiologic state of the patient. For example, to reduce the level of wakefulness, one must not start with a red light signal and a high pitch audio signal if the patient is relaxed. This would only lead to an unnecessary loss of time because a red light signal and a high pitch audio signal would first excite the nervous system and raise the level of wakefulness, after which a change of color and pitch would only bring wakefulness down to the original level.

Optimum results are achieved by using the visible optical spectrum and pitches of 50 to 1,500 Hz.

A patient is made to fall asleep by reducing the light wavelength and lowering the pitch of the audio signal with respect to the initial levels.

The level of wakefulness is rasied by increasing the light wavelength and raising the pitch of the audio signal with respect to the initial levels.

The method according to the invention is carried out with the aid of a device comprising a controlled audio pulse pacemaker intended to expose the patient to the effects of audio signals of a desired frequency, amplitude and duration; a controlled light pulse pacemaker intended to expose the patient to the effects of light signals of variable chromaticity, amplitude, frequency and duration; a pulse repetition setting unit intended to set the pulse repetition frequency for the light and audio pacemakers; a pulse amplitude setting unit intended to set the pulse amplitude for the pacemakers; a pulse duration setting unit intended to set the pulse duration for the pacemakers; modulators in a number equal to the number of light signals produced by the light pacemaker, their inputs being separately connected to outputs of the pacemakers, and their outputs being connected to said pacemakers to synchronously vary the frequency, duration and amplitude of the light and audio signals; a switch intended to switch in a predetermined order the modulators and units for setting the chromaticity of light signals and tonality of audio signals; a control unit intended to control said setting units by producing signals to control the pattern of varying the functional state of the central nervous system, depending on the task to be performed, which is either to produce a soporific effect or to raise the level of wakefulness; and a programming or storage unit intended to receive information on changes of the biorhythm according to a change state of the central nerous system, which is connected to the pulse frequency, amplitude and duration setting units of the light and audio pacemakers and serves to produce a signal whereby the frequency, amplitude and duration of pulses are changed by the respective setting units, depending on the biorhythm frequency within specified time intervals.

BRIEF DESCRIPTION OF THE DRAWINGS

Other objects and advantages of the present invention will become more apparent from a consideration of the following detailed description of a preferred embodiment thereof, taken in conjunction with the accompanying drawings, wherein.

DETAILED DESCRIPTION OF THE INVENTION

Figure 1:
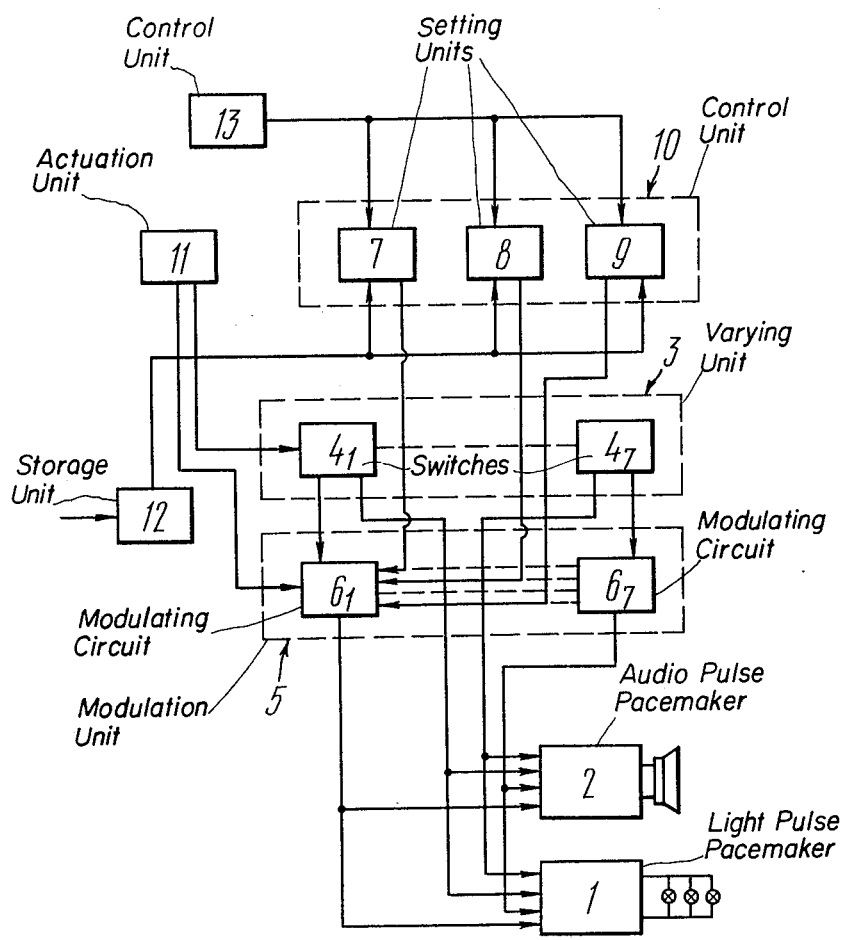
FIG. 1 is a block diagram of a device for acting on the central nervous system, in accordance with the invention.

Consider now FIG. 1 which is a block diagram of the device for controlling the state of the central nervous system in accordance with the invention. The device comprises a controlled light pulse pacemaker 1, a controlled audio pulse pacemaker 2, and a varying unit 3 for varying the chromaticity and pitch of the pacemakers 1 and 2, respectively. The unit 3 comprises flip-flops, of which more details are given below, and switches 4 in a number equal to the number of colors and tonalities chosen for action upon the patient. The embodiment under review makes use of the seven colors of the white light spectrum, i.e. red, orange, yellow, green, blue, indigo and violet, and of seven tonality ranges of audio signals. (Thus FIG. 1 shows switches $4_1$ to $4_7$.) The device further includes a chromaticity and tonality modulation unit 5 which contains seven indentical modulators or modulating circuits $6_1$ to $6_7$. Thus the circuits 6 are in a number equal to the number of light and audio signals. The circuits 6 are intended to carry out amplitude and frequency modulation of these signals.

The circuits 6 of the modulation unit 5 are controlled by setting units 7, 8 and 9 incorporated in a control unit 10. The setting unit 7 serves to control the frequency of rhythmic signals; the setting unit 8 serves to control the amplitude of rhythmic signals, i.e. the volume of sound and brightness of light; and the setting unit 9 serves to control the duration of the rhythmic signals.

The device further includes an actuation unit 11 whose purpose is to actuate the switches 4. The switches 4 are intended to select the original color and tonality and carry over to the next color or tonality.

The device of this invention is meant to control the functional state of the central nervous system of both sleeping and wakeful patients. To perform these functions, it is provided with a control unit 13 intended to control the setting units. The unit 13 forms a saw-toothed signal. The setting units of the unit 10 are actuated by the rising or falling edges of the saw-toothed signals to form signals for sleeping patients or those awake, respectfully.

The parameters of the output signals of the setting units of the unit 10 are determined by biorhythms specified, for example, by an electroencephalogram. For this purpose, the device according to the invention is provided with a storage or programming unit 12 intended to supply information on biorhythms.

The programming or storage unit 12 stores information on biorhythms, including the frequency of biorhythms in the initial state and variations of this frequency occurring as the patient falls asleep or as the wakefulness level is raised. During the rhythmic action upon the patient, the information on biorhythms is reproduced as a program of changes of the frequency, amplitude and duration of the rhythmic signals. The unit 12 is, preferably, a recording and reproducing magnetic device, such as a miniature tape recorder, a set of magnetic memory cells, etc.

Figure 4:
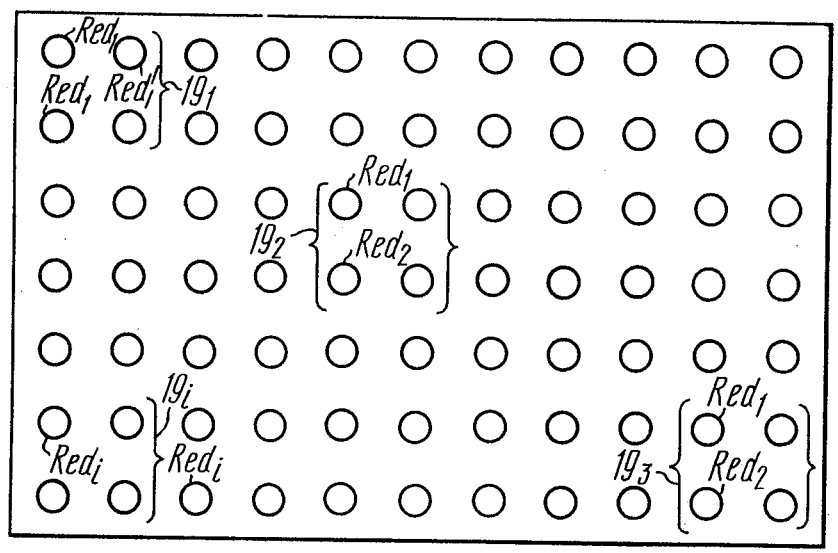
FIG. 4 is a plan view of the panel and lamps of the light pacemaker in accordance with the invention.
Figure 5:
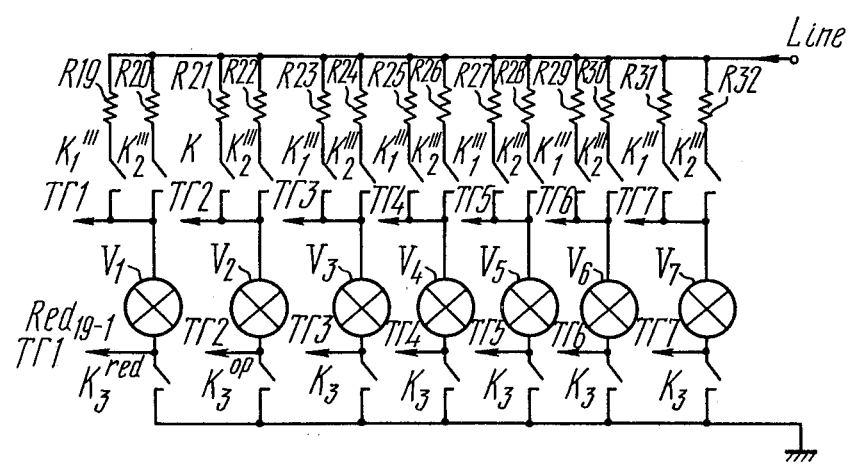
FIG. 5 is a wiring diagram showing the connection of the lamps of FIG. 4, wherein groups of lamps are shown conventionally.

Consider now a detailed description of each of the above-mentioned units and connections between them. The light pacemaker (FIG. 4) comprises a plurality of monochrome lamps, such as a group of red lamps $19_1$, . . . , $19_i$ which are uniformly spaced over the entire surface of a screen. Outputs of these groups of lamps are connected to switching contacts of the switch $4_i$ and pulsatory contacts $K_3$ of the modulating circuit or modulator $6_1$ (FIG. 5); in FIG. 4, each group of lamps is conventionally designated as V. The color saturation is varied by switching the lamps of each color, which have different turn-on thresholds. The pitch is varied within the range of each color by the modulator as will be shown below.

Figure 2:
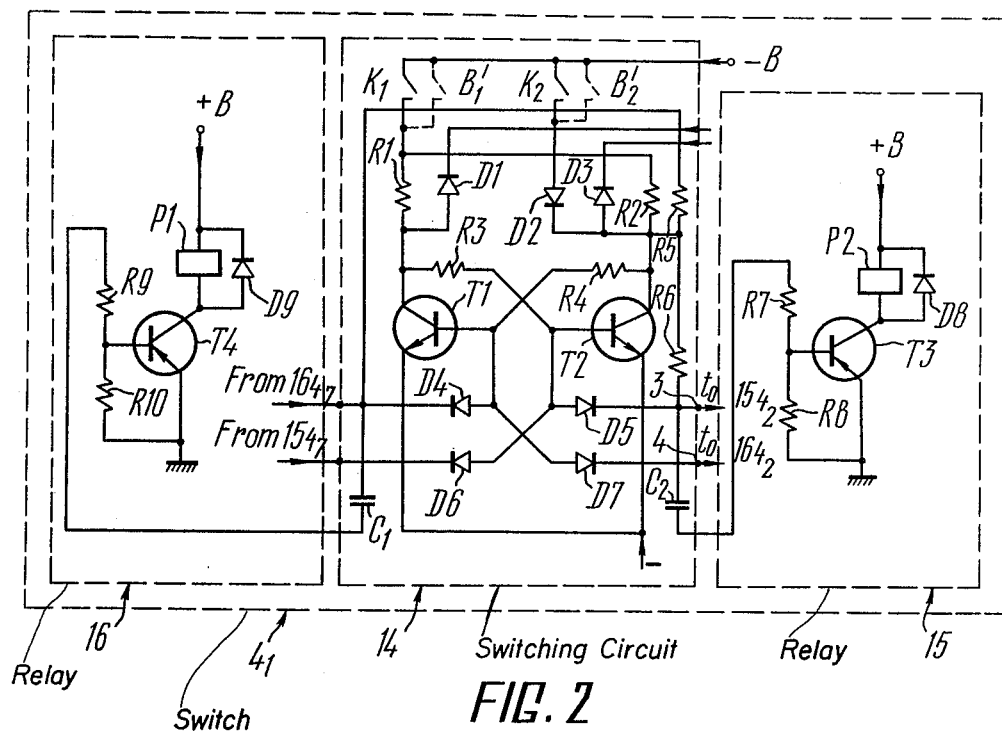
FIG. 2 is an electrical schematic diagram of the switch with electronic relays of the device of FIG. 1.
Figure 3:
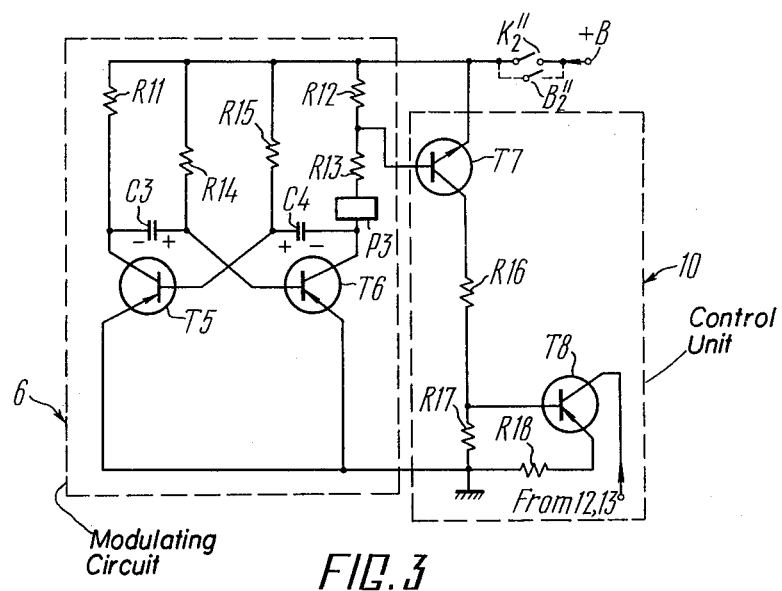
FIG. 3 is an electrical schematic diagram of the modulator with frequency, amplitude and duration setting units, in accordance with the invention.

All the seven modulators 6 are identical, so FIG. 3 shows only one such modulator 6 which is an asymmetrical multivibrator built of transistors T5 and T6. The collector circuits of the transistors T5 and T6 contain resistors R11, R12 and R13; the base circuits of the transistor T5 and T6 contain resistors R14 and R15. The collector of the transistor T5 is connected to the base of the transistor T6 via a capacitor C3; the collector of the transistor T6 is connected to the base of the transistor T5 via a capacitor; C4 and the positive terminals of the capacitors C3 and C4 are connected to the bases of the transistors T5 and T6. A power source "+B" feeds current to the modulator (units $4_1$ through $4_7$) via a contact $K_2''$ of an electromagnetic relay P2 which has three groups of contacts (FIG. 2). The contact $K_2''$ of this relay P2 connects the power source "+B" to the collector circuits of the transistors T5 and T6 and to the emitter circuit of a transistor T7; a contact $K_1''$ connects the power source "+B" to a respective lamp ($V_1$ through $V_7$) of the light pacemaker 1 and to a respective tone generator (not shown) of the audio pacemaker 2. The winding of the electromagnetic relay P3 is connected to the collector circuit of the transistor T6; as pulsed current is applied to it by the multivibrator, it makes the contact K3 pulsate. Also placed in the collector circuit of the multivibrator is a circuit composed of transistors T7 and T8 and resistors R16, R17 and R18 which determine the operating conditions of said transistors T7 and T8 (see arrow 10 in FIG. 3). This circuit performs the functions of the setting units 7, 8 and 9 in that it varies the frequency, amplitude and duration of the signals (the details are given below); circuitry-wise, it is combined with the modulator. The units 12 and 13 apply a.c. voltage to the collector of the transistor T8.

FIG. 2 shows the switch $4_1$ of the group of switches $4_1, \ldots, 4_i$. The switch $4_1$ comprises a reversible flip-flop switching circuit 14 with electronic relays 15 and 16 connected to its output. The electronic relay 15 is actuated when the device is used to make a patient fall asleep; the relay 16 is actuated when treating one who is awake. The flip-flop switching circuit 14 (FIG. 2) comprises transistors T1 and T2 with resistors R1 and R2 placed in their respective collector circuits. The collector of the transistor T1 is connected to the base of the transistor T2 via a resistor R3. The collector of the transistor T2 is connected to the base of the transistor T1 via a resistor R4. The base of the transistor T2 is connected to two adjacent circuits, i.e. to the base of the left transistor $T2_2$ of the next flip-flop switching circuit (for example, for switching over from the red section to the orange section), the connection being effected via a diode D5; the base of the transistor T2 is also connected via a diode D6 to the base of the left triode of the previous switching circuit $T2_7$. The base of the transistor T1 is similarly connected to the bases of the triodes of the previous and next circuits via the diodes D7 and D4. Each of the discharge capacitors C1 and C2 has one lead connected via diodes D4 and D5, respectively, to the base of the transistors T1 and T2, respectively; the first leads of the capacitors C1 and C2 are also connected via resistors R5 and R6 to the collector of the triode T2 connected to the power source "−B" via the diode D2 and contact K2 of the electronic relay 15. Diodes D1 and D3 are connected in the collector circuits of the triodes T1 and T2 and intended to effect a drop of voltage at the collectors of these triodes. From the power source "−B", voltage is applied via contacts K1 and K2 of electronic relays 1 and 2 to the collectors of the triodes T1 and T2.

The circuitry of the electronic relays is well known to those skilled in the art. Each of these relays comprises a triode T3 (see reference numeral 15), resistors R7 and R8, which determine the operation threshold of the electronic relay, an electromagnetic relay P2 connected in the collector circuit of the triode T3, and a diode D8 which shunts the winding of the electromagnetic relay P2. As stated above, the electromagnetic relay P2 has three pairs of contacts ($K_2$, $K_2''$ and $K_2'''$).

The control unit 13 is a conventional saw-toothed wave generator built around a transistor (not shown). The actuation unit 11 is a switching circuit comprising two electronic relays (not shown) connected as are those of the unit 3 (FIG. 2, reference numerals 15 and 16). The operation thresholds of these electronic relays are selected as follows: rising saw-toothed voltage, produced by the unit 13, actuates the electronic relay with a lower operation threshold, whereas falling saw-toothed voltage actuates the relay having a higher operation threshold. Thus the contacts of the electronic relay automatically bring into play either the first flip-flop switching circuit $4_1$ which corresponds to red and is used in the case of a patient who is to be relaxed, or the last circuit $4_7$ which corresponds to violet and is used to treat a patient who is awake and has to be stimulated. The unit 11 includes a set of pushbutton contacts $B_1'$, $B_2'$, ..., etc., and $B_2''$, which are connected in the flip-flop switching circuits in parallel with the contacts $K_1$, $K_2$, etc. and contacts $K_1''$, $K_2''$, etc. of the modulator 5. The pushbuttons are arranged on a control panel.

Consider now operation of the device in accordance with the invention. Let it be assumed that a patient needs relaxation. He or she lies on a bed or couch (not shown) and is told to choose a color and tonality which seem to be the most pleasing at the moment and with which the séance of treatment is to be started. Prior to exposing the patient to the effects of rhythmic signals, the initial frequency of the predominant rhythm of the electroencephalogram (the respiration rate and heart rate) is recorded. Initially, the action of rhythmic signals is to be in keeping with this original frequency.

Suppose the patient chooses the yellow color (the wavelength is 580 nanometers) and a pitch of 600 Hz. The control unit 13 is turned on and adjusted to operate so as to make the patient fall asleep. The yellow color button on the control panel of the actuation unit 11 is pushed to close the contact $B_2''$ (FIG. 3) which is placed in parallel with the contact $K_2''$ and intended to apply voltage of the power source "+B" to the units 6 and 10 (FIG. 3); the pushbutton also closes the contact $B_2'$ which is connected in parallel with the contact $K_2$ and intended to apply "−B" voltage to the switch $4_3$ (reference numeral 14 of FIG. 2). This turns on the modulator $6_3$. Under the action of the current in the winding of the electromagnetic relay $P3_3$, the contacts $K3_3$ vibrate and break the circuit of the lamps in the light pacemaker 1 and that of the contacts of the tone generator of the audio pacemaker 2, which correspond to the yellow color. The control unit 10 performs frequency, amplitude and duration modulation of light and sound. The initial operating conditions of the unit 10 are set by a voltage corresponding to the initial predominant frequency of the electroencephalogram (the respiration rate, electrocardiogram), which is applied from the unit 11 to the collector of the transistor of the unit 10.

As stated above, the saturation of color is variable because the lamps possess different turn-on thresholds.

As the modulator $6_3$ of the modulation unit 5 is put into operation, so is the right part of the flip-flop switching circuit 14 of the switch 4₃. The transistor T2 of the circuit 14 is off, thereby causing capacitor C2 to slowly discharge, whereafter the electronic relay 15 is actuated. The capacitor C2 discharges mainly through the circuit R7–R8 of the transistor T3 of the electronic relay 15; as a result, the transistor T3 is driven into conduction and actuates the electromagnetic relay P2. The discharge of the capacitor C2 of the yellow color circuit is followed by a closure of the contacts K₂ connected to the collector of the right transistor of the green color flip-flop switching circuit. The contact K₂″ turns on the green color modulator 6₄; the contacts K₁‴ and K₂‴ turn on the green lamp V₄ and the respective tone generator (not shown). At the same time the contact K₂ of the modulator 6₃ is broken, whereas the contact K₂ of the modulator 6₄ is made. The green color modulator 6₄ is brought into action and makes the contacts K3₄ pulsate due to the pulsed current passed through the winding of the electromagnetic relay P3₄; thus the lamps V₄ and the respective tone generator are repeatedly turned on for short periods of time.

Variations of voltage applied from the storage or programming unit 12 lead to changes of the resistance of the circuit T8, R16, R17, R18 and T7 (FIG. 2). If the patient is supposed to fall asleep, the frequency and amplitude of the signal decrease, while its duration increases; to stimulate the patient, the resistance of the above-mentioned circuit increases and so do the frequency and amplitude of the signal, but the duration of the signal decreases. Changing the amplitude of the signal is used to successively turn on lamps of different color saturation. Color saturation of the lamps is different because they have different operation thresholds, which, in turn, is due to the selection of different values of damping resistors connected in the supply circuits of these lamps.

Operation of all the other units, corresponding to other colors and pitches, is similar to what is stated above. The signal of the last unit actuates the yellow color unit, and the foregoing sequence of events is repeated.

The above description deals with the case when the level of wakefulness has to be brought down. The level of wakefulness is brought up by using the same principle, but in this case the relay units 16 are brought into play.

In principle, the method for controlling the functional state of the central nervous system in accordance with the invention consists in exposing a patient to simultaneous effects of rhythmic audio and light signals of a certain frequency, amplitude and duration. First, one has to determine the change of the frequency of biorhythms in the course of the transition to one of the extreme stable states of the central nervous system, which is done by means by electroencephalography and electrocardiography, as well as by measuring the resipiration rate. The foregoing description shows how the data on biorhythms is collected in the case where the patient is supposed to fall asleep. The final step of the preparation stage is to select initial light and audio signals for each interval of change of the biorhythm.

Normally it is best to let the patient choose the initial light and audio signals. If the level of wakefulness has to be brought down, it is best to start the rhythmic action with either yellow, orange or green.

The foregoing description is concerned with a case when the action is started with the yellow color.

The next step is to synchronously vary the frequency, amplitude and duration of the rhythmic signals within the established intervals of frequency variations of the biorhythms. As these intervals change, so do the tonality of the audio signal and the chromaticity of the light signal.

This is done by the control unit 10 which applies voltage to the modulation unit 5 so as to control their operation with due regard for operation of the programming or storage unit 12 and the control unit 13. The change of tonality and chromaticity is effected by the unit 5; the use of lamps with different turn-on thresholds has already been mentioned above.

The following examples will serve to illustrate the invention.

EXAMPLE 1

Patient K, a turner by profession, complained during his visit to a neurologist that he had difficulty in falling asleep. His predominant biorhythm was determined from an electroencephalogram taken before the course of treatment. Of all the light and audio signals, the patient selected the yellow color (580 nanometers) and an audio signal of 600 Hz and 62 db. The séance of rhythmic stimulation lasted 25 minutes. The initial frequency was 10 times the predominant frequdncy of the electroencephalogram. Further change of frequency was done automatically according to the changing electroencephalogram of the patient as he was falling asleep.

Although the treatment was performed at 11 a.m., the patient slept better after it. He went to bed at 10:30 p.m., and it took him only five minutes to fall asleep. His sleep became normal after two séances, although it took two more séances to make sure that the treatment was totally effective. After the course of treatment consisting of four séances, K was under observation over a period of two years and never complained of being unable to fall asleep. No undesired side effects were observed and the patient slept much better than before the treatment.

EXAMPLE 2

Patient V, a driver, complained of sleepiness which interfered with his work. The mean value of the predominant biorhythm was determined from an electroencephalogram. Of all the light and audio signals, the patient chose the green color (540 nanometers) and an audio signal of 400 Hz and 60 db. The initial rhythmic stimulation frequency was ten times the dominating frequency of the electroencephalogram taken prior to the séance. Subsequent change of the rhythmic signals frequency was carried out automatically in accordance with the predominant rhythm of the electroencephalogram measured as the level of wakefulness was being brought up. The first séance lasted 25 minutes; each next séance was five minutes longer than the previous. It took three séances to eliminate sleepiness compliness completely; one more seance was given to stabilize the positive effect. After the course of treatment consisting of four séances, V was observed during 18 months. There were no more complaints from the patient and no negative side effects were observed.

While particular embodiments of the invention have been shown and described, various modifications thereof will be apparent to those skilled in the art. It is therefore not intended that the invention should be limited to the disclosed embodiments or details thereof; it is understood that departures may be made from the disclosed embodiments within the spirit and scope of the invention as defined in the claims.

For example, the function of the light source of the controlled light pulse pacemaker can be effectively performed by a semiconductor laser which features controlled chromaticity over the entire optical range.

The function of the light source of the light pulse pacemaker can also be performed by a screen of ferroelectric ceramics, whose color is varied depending on the voltage applied thereto by the modulator.

What is claimed is:

1. A method for controlling the functional state of the central nervous system through exposure of a patient to simultaneous effects of a rhythmic audio signal and a rhythmic light signal, comprising the steps of: determining the change of the biorhythm frequency in the course of a transition to one of the extreme stable states of the central nervous system; setting an initial light signal and an initial audio signal; synchrononously varying the frequency, amplitude and duration of the rhythmic audio and light signals within the established intervals of frequency change of biorhythms; and varying the pitch of the audio signal and the color of the light signal in accordance with the change of the intervals.

2. A method as claimed in claim 1 wherein the color and pitch of the initial signals are chosen by the patient.

3. A method as claimed in claim 1, wherein the color of the light signal is varied within the visible optic spectrum, and the pitch of the audio signal is selected within the range of 50 to 1,500 Hz.

4. A method as claimed in claim 1, wherein the patient is made to fall asleep by reducing the light wavelength with respect to the original wavelength and lowering the pitch of the audio signal with respect to the original pitch.

5. A method as claimed in claim 1, wherein the patient is stimulated by increasing the light wavelength with respect to the original wavelength and raising the pitch of the audio signal with respect to the original pitch.

6. A method as claimed in claim 4, wherein the wavelength of the light signal is reduced from 770 nanometers to 380 nanometers, and the pitch of the audio signal is reduced from 800 to 200 Hz.

7. A method as claimed in claim 5, wherein the wavelength of the light signal is increased from 380 nanometers to 770 nanometers, and the pitch of the audio signal is raised from 200 to 800 Hz.

8. A method as claimed in claim 1, wherein the color of the light signal and the pitch of the audio signal are repeatedly varied till a stable state of the central nervous system is reached.

9. A device for controlling the functional state of the central nervous system, comprising a controlled audio pulse pacemaker to expose a patient to the effects of audio signals of a desired frequency, amplitude and duration; a controlled light pulse pacemaker to expose a patient to the effects of light signals of a variable color, amplitude, frequency and duration; a first setting unit setting the pulse repetition frequency of the light and audio pacemakers; a second setting unit setting the duration of pulses produced by said light and audio pacemakers; a third setting unit setting the amplitude of pulses produced by said light and audio pacemakers; modulators in a number equal to the number of light signals of the light pulse pacemaker, said modulators having inputs separately connected to outputs of said setting units, and outputs connected to said pacemakers in order to synchronously vary the frequency, duration and amplitude of the light and audio signals; a switch switching in a preselected order the color modulators of the light signals source and the pitch modulators of the audio signals source; a control unit controlling said setting units and producing signals to control the modulators of the light and audio signals sources, depending on the variations of the level of the functional state of the central nervous system; a programming unit receiving information on changes of the patient's biorhythm caused by changes of the functional state of the central nervous system, said programming unit being connected to the setting units to form a signal for a change of the frequency, amplitude and duration of the signals by said setting units depending on the biorhythm frequency over given time intervals.

10. A device as claimed in claim 9, wherein the controlled light pulse pacemaker includes a set of electric lamps of different colors, lamps in each group of lamps of the same color having different turn-on thresholds so as to vary the saturation of color.

11. A device as claimed in claim 9, wherein the light wavelengths vary from 770 to 380 nanometers, and the pitch of audio signals varies from 800 to 200 Hz.

12. A device as claimed in claim 9, wherein the control unit which controls the setting units is a saw-toothed voltage generator.

13. A device as claimed in claim 9, wherein the first, second and third setting units each include a first transistor and a second transistor, the base of the first transistor being connected to the collector of the second transistor via a frequency divider, the collector of the first transistor being connected to the saw-toothed voltage source and to the programming unit, the emitter of the second transistor being connected to a power source, and the base of the second transistor being connected to the output of the setting units and to the modulators.

14. A device as claimed in claim 9, wherein the switch for switching the modulators, the lamps of the light pulse pacemaker and a tone generator of the audio pulse pacemaker is a flip-flop switching circuit having two outputs connected to electronic relays, one of which being actuated when the patient is to be made to fall asleep, and the other of which being actuated when the patient is to be stimulated.

* * * * *